United States Patent
Yamamoto et al.

(10) Patent No.: US 11,826,473 B2
(45) Date of Patent: Nov. 28, 2023

(54) ORALLY DISINTEGRATING TABLET COATED WITH FILM

(71) Applicant: SAWAI PHARMACEUTICAL Co., Ltd., Osaka (JP)

(72) Inventors: Hiroyuki Yamamoto, Osaka (JP); Ayane Natsume, Osaka (JP); Yuki Nishikawa, Osaka (JP); Michinori Oikawa, Osaka (JP); Hiroaki Kikuoka, Osaka (JP)

(73) Assignee: SAWAI PHARMACEUTICAL CO., LTD., Osaka (JP)

( * ) Notice: Subject to any disclaimer, the term of this patent is extended or adjusted under 35 U.S.C. 154(b) by 0 days.

(21) Appl. No.: 16/244,791

(22) Filed: Jan. 10, 2019

(65) Prior Publication Data
US 2019/0231700 A1    Aug. 1, 2019

(30) Foreign Application Priority Data
Jan. 11, 2018   (JP) .................... 2018-002490

(51) Int. Cl.
*A61K 9/42* (2006.01)
*A61K 9/28* (2006.01)

(52) U.S. Cl.
CPC .......... *A61K 9/2866* (2013.01); *A61K 9/2813* (2013.01); *A61K 9/2826* (2013.01)

(58) Field of Classification Search
CPC ... A61K 9/2054; A61K 9/2866; A61K 9/2813
See application file for complete search history.

(56) References Cited

U.S. PATENT DOCUMENTS

| | | | |
|---|---|---|---|
| 2002/0015733 A1* | 2/2002 | Flashner-Barak | A61P 3/14 424/484 |
| 2006/0188570 A1* | 8/2006 | Batra | A61K 9/2018 424/464 |
| 2009/0202636 A1* | 8/2009 | Beso | A61K 31/5415 424/475 |
| 2010/0015239 A1* | 1/2010 | Ahmed | A61K 9/5026 424/497 |
| 2011/0280942 A1* | 11/2011 | Schad | A23G 3/343 106/203.3 |
| 2012/0189696 A1* | 7/2012 | Yoshida | A61K 9/2054 424/465 |
| 2015/0104512 A1 | 4/2015 | Ognibene et al. | |

FOREIGN PATENT DOCUMENTS

| | | |
|---|---|---|
| JP | 2000-44464 A | 2/2000 |
| JP | 2004-217652 A | 8/2004 |
| JP | 2006-111601 A | 4/2006 |
| JP | 2010248106 A | 11/2010 |
| JP | 4972563 B2 | 7/2012 |
| JP | 2015-514786 A | 5/2015 |
| JP | 2018-111668 A | 7/2018 |
| WO | 2014157264 A1 | 2/2017 |
| WO | 2015122477 A1 | 3/2017 |

OTHER PUBLICATIONS

Office Action dated Aug. 2, 2022 for corresponding Japanese Patent Application No. 2019-002896, along with an English machine translation (8 pages).

* cited by examiner

*Primary Examiner* — Kyle A Purdy
(74) *Attorney, Agent, or Firm* — HAUPTMAN HAM, LLP

(57) ABSTRACT

Provided is an orally disintegrating tablet film-coated with a composition for film coating containing hypromellose and hydroxypropyl cellulose but not containing a plasticizer.

2 Claims, 3 Drawing Sheets

FIG. 1A

| Aim of blending | Additive agent | Comparative Example 1 HPMC/HPC/PG= 10/0/3 | | Comparative Example 2 HPMC/HPC/PG= 10/3/2 | | Comparative Example 3 HPMC/HPC/PG= 10/0/0 | | Comparative Example 4 HPMC/HPC/PG= 0/10/0 | |
|---|---|---|---|---|---|---|---|---|---|
| | | mg/Tab | % | mg/Tab | % | mg/Tab | % | mg/Tab | % |
| Base | HPMC | 2.25 | 66.2 | 1.80 | 52.9 | 2.90 | 85.3 | - | - |
| | HPC | - | - | 0.45 | 13.2 | - | - | 2.90 | 85.3 |
| Plasticizer | PG | 0.65 | 19.1 | 0.65 | 19.1 | - | - | - | - |
| Coloring agent | Titanium oxide | 0.0375 | 1.1 | 0.0375 | 1.1 | 0.0375 | 1.1 | 0.0375 | 1.1 |
| Lubricant | Talc | 0.125 | 3.7 | 0.125 | 3.7 | 0.125 | 3.7 | 0.125 | 3.7 |
| Corrigent | Erythritol | 0.3175 | 9.3 | 0.3175 | 9.3 | 0.3175 | 9.3 | 0.3175 | 9.3 |
| Sweetener | Sucralose | 0.02 | 0.6 | 0.02 | 0.6 | 0.02 | 0.6 | 0.02 | 0.6 |
| | Total | 3.40 | 100.0 | 3.40 | 100.0 | 3.40 | 100.0 | 3.40 | 100.0 |

<End-point>

| | | Comparative Example 1 | Comparative Example 2 | Comparative Example 3 | Comparative Example 4 |
|---|---|---|---|---|---|
| | Manufacturability (Pairing) | No | No | No | Yes |
| Stability under humidity 25°C, 75%RH, 16 h | Thickness of tablet (mm) initial | 3.48 | 3.48 | 3.49 | 3.48 |
| | Thickness of tablet (mm) | 3.88 | 3.87 | 3.92 | 3.97 |
| | Increase rate (%) | 11% | 11% | 12% | 14% |
| | Cracking in film | Yes | Yes | Yes | - |
| Feeling of administration | Mouthfeel of film when taking | ○ | ○ | ○ | ○ |
| | Taste of film | ○ | ○ | ○ | ○ |
| | Dissolution time of film | 6 to 7 | 5 to 6 | 7 to 8 | 6 to 8 |

FIG. 1B

| Blending ratio of film base, plasticizer | | Example 1 HPMC/HPC/PG= 10/2.5/0 | | Example 2 HPMC/HPC/PG= 10/10/0 | | Example 3 HPMC/HPC/PG= 2.5/10/0 | | Example 4 HPMC/HPC/PG= 10/0.5/0 | | Example 5 HPMC/HPC/PG= 0.5/10/0 | |
|---|---|---|---|---|---|---|---|---|---|---|---|
| Aim of blending | Additive agent | mg/Tab | % | mg/Tab | % | mg/Tab | % | mg/Tab | % | mg/Tab | % |
| Base | HPMC | 2.32 | 68.2 | 1.45 | 42.6 | 0.58 | 17.1 | 2.76 | 81.2 | 0.14 | 4.1 |
| | HPC | 0.58 | 17.1 | 1.45 | 42.6 | 2.32 | 68.2 | 0.14 | 4.1 | 2.76 | 81.2 |
| Plasticizer | PG | - | - | - | - | - | - | - | - | - | - |
| Coloring agent | Titanium oxide | 0.0375 | 1.1 | 0.0375 | 1.1 | 0.0375 | 1.1 | 0.0375 | 1.1 | 0.0375 | 1.1 |
| Lubricant | Talc | 0.125 | 3.7 | 0.125 | 3.7 | 0.125 | 3.7 | 0.125 | 3.7 | 0.125 | 3.7 |
| Corrigent | Erythritol | 0.3175 | 9.3 | 0.3175 | 9.3 | 0.3175 | 9.3 | 0.3175 | 9.3 | 0.3175 | 9.3 |
| Sweetener | Sucralose | 0.02 | 0.6 | 0.02 | 0.6 | 0.02 | 0.6 | 0.02 | 0.6 | 0.02 | 0.6 |
| Total | | 3.40 | 100.0 | 3.40 | 100.0 | 3.40 | 100.0 | 3.40 | 100.0 | 3.40 | 100.0 |

<End-point>

| | Example 1 | Example 2 | Example 3 | Example 4 | Example 5 |
|---|---|---|---|---|---|
| Manufacturability (Pairing) | No | No | No | No | Small portion |
| Stability under humidity 25°C, 75%RH, 16 h | Thickness of tablet (mm) initial | 3.48 | 3.48 | 3.48 | 3.54 | 3.49 |
| | Thickness of tablet (mm) | 3.9 | 3.89 | 3.98 | 3.85 | 3.85 |
| | Increase rate (%) | 12% | 12% | 14% | 9% | 10% |
| | Cracking in film | No | No | No | No | No |
| Feeling of administration | Mouthfeel of film when taking | ○ | ○ | ○ | ○ | ○ |
| | Taste of film | ○ | ○ | ○ | ○ | ○ |
| | Dissolution time of film | 6 to 8 | 6 to 8 | 6 to 8 | 8 to 10 | 5 to 6 |

FIG. 2

| Aim of blending | | Example 4 | | Example 5 | | Example 6 | | Comparative Example 5 | | Comparative Example 6 | |
|---|---|---|---|---|---|---|---|---|---|---|---|
| Blending ratio of titanium oxide to the total weight of HPMC and HPC (% w/w) | | 5.9 | | 11.7 | | 23.4 | | 46.9 | | 58.6 | |
| | Additive agent | mg/Tab | % | mg/Tab | % | mg/Tab | % | mg/Tab | % | mg/Tab | % |
| Base | HPMC | 2.32 | 65.7 | 2.32 | 62.7 | 2.32 | 57.4 | 2.32 | 49.1 | 2.32 | 45.8 |
| | HPC | 0.58 | 16.4 | 0.58 | 15.7 | 0.58 | 14.3 | 0.58 | 12.3 | 0.58 | 11.5 |
| Coloring agent | Titanium oxide | 0.17 | 4.8 | 0.34 | 9.2 | 0.68 | 16.8 | 1.36 | 28.8 | 1.70 | 33.6 |
| Lubricant | Talc | 0.125 | 3.5 | 0.125 | 3.4 | 0.125 | 3.1 | 0.125 | 2.6 | 0.125 | 2.5 |
| Corrigent | Erythritol | 0.318 | 9.0 | 0.318 | 8.6 | 0.318 | 7.9 | 0.318 | 6.7 | 0.318 | 6.3 |
| Sweetener | Sucralose | 0.02 | 0.6 | 0.02 | 0.5 | 0.02 | 0.5 | 0.02 | 0.4 | 0.02 | 0.4 |
| Total | | 3.53 | 100.0 | 3.70 | 100.0 | 4.04 | 100.0 | 4.72 | 100.0 | 5.06 | 100.0 |

| End-point | Example 4 | Example 5 | Example 6 | Comparative Example 5 | Comparative Example 6 |
|---|---|---|---|---|---|
| Thickness of tablet (mm) initial | 3.49 | 3.47 | 3.49 | 3.52 | 3.50 |
| Thickness of tablet (mm) | 4.28 | 4.25 | 4.22 | 4.19 | 4.21 |
| Increase rate (%) of thickness of orally disintegrating tablet under high humidity | 23% | 22% | 21% | 19% | 20% |
| Stability under humidity 25°C, 90%RH, 5 h — Cracking in film | No | No | No | Yes | Yes |
| Dissolution time of film (seconds) | 5 to 6 | 5 to 6 | 6 to 7 | 7 to 8 | 6 to 7 |

ORALLY DISINTEGRATING TABLET COATED WITH FILM

CROSS REFERENCE TO RELATED APPLICATIONS

This application is based upon and claims the benefit of priority from the prior Japanese Patent Application No. 2018-002490, filed on Jan. 11, 2018 the entire contents of which are incorporated herein by reference.

FIELD

The present invention relates to a film-coated orally disintegrating tablet. In particular, the present invention relates to a film-coated orally disintegrating tablet that is short in dissolution time, is excellent in spreadability, and is excellent in versatility.

BACKGROUND

An orally disintegrating tablet is an oral solid preparation quickly disintegrating intraorally in about 30 seconds or in less 30 seconds only with intraoral saliva or with a small amount of water. Since the orally disintegrating tablet quickly disintegrates, the orally disintegrating tablet is a preparation easy for a patient to take, and particularly the needs of elderly persons or children who have poor swallowing ability for the orally disintegrating tablet is growing.

Generally, it is common practice to apply film coatings in oral solid preparations such as tablets or granules in order to maintain hardness or suppress hygroscopicity. Further, the film coating is applied to protect or stabilize an active ingredient from an environmental factor, for example, humidity or light.

In addition, when the active ingredient is a highly active ingredient for an anticancer drug, a hormone acting agent or the like, let alone during the course of distribution, the exposure of healthcare professionals in medical sites to the highly active ingredients should be avoided, and unnecessary exposure of a patient him/herself to the high active ingredient is undesirable. The film coating is also thought to be useful from the aspect of safety measures to such exposure.

On the other hand, a film for coating the orally disintegrating tablet is required to quickly dissolve in the oral cavity of a patient. Further, since many orally disintegrating tablets are low in tablet hardness and have hygroscopicity, the film is required to be a film having enough spreadability to endure swelling of a tablet.

Further, in general, a formulation of a film portion is composed of film base and plasticizer, and the plasticizer contributes to spreadability and homogeneity of the film and is frequently used in a film formulation.

For example, Japanese Patent No. 4972563 discloses coating of a coating layer containing a film base such as hydroxypropyl methylcellulose (HPMC) or hydroxypropyl cellulose (HPC), and propylene glycol (PG), Internation Publication WO 2015/122477 discloses a composition for film coating containing a film coating base such as hydroxypropyl methylcellulose, and plasticizer, Internation Publication WO 2014/157264 discloses a film formulation containing cellulosic resin and polyethlyene glycol (PEG), and Japanese Patent Application Laid-Open No. 2010-248106 discloses a film formulation containing a water-soluble polymer and PEG.

The film has spreadability and plasticity by containing a plasticizer such as PEG, but a film formulation containing the plasticizer cannot be used for a tablet containing an active ingredient whose stability is impaired by contacting the plasticizer. Accordingly, the development of a film formulation excellent in spreadability and excellent in versatility has been desired.

SUMMARY

An object of the present invention is to provide a film-coated orally disintegrating tablet. In particular, another object of the present invention is to provide a film-coated orally disintegrating tablet that is short in dissolution time, is excellent in spreadability, and is excellent in versatility.

In addition, a still another object of the present invention is to provide a film-coated orally disintegrating tablet that can also be used in an tablet containing an active ingredient whose storage stability is impaired by coming in contact with the plasticizer.

According to one embodiment of the present invention, there is provided a film-coated orally disintegrating tablet coated with a composition for film coating containing hypromellose and hydroxypropyl cellulose but not containing a plasticizer.

The hydroxypropyl cellulose may be contained in a ratio of less than 1:20 in a weight ratio when the hypromellose is 1.

The hydroxypropyl cellulose may be contained in a ratio of 1:4 or less in a weight ratio when that the hypromellose is 1.

A blending ratio of the hypromellose to the hydroxypropyl cellulose in the composition for film coating may be in a range from 4:1 to 1:4 in a weight ratio.

The composition for film coating tablet may contain titanium oxide to a total weight of the hypromellose and the hydroxypropyl cellulose in a ratio of 23.4% by weight or less.

BRIEF DESCRIPTION OF DRAWINGS

FIG. 1A is tables showing formulations of compositions for film coatings and physical properties or the like of preparations of film-coated orally disintegrating tablets according to comparative examples, FIG. 1B is tables showing formulations of compositions for film coatings and physical properties or the like of preparations of film-coated orally disintegrating tablets according to examples of the present invention, and FIG. 2 is tables showing physical properties or the like of preparations of the film-coated orally disintegrating tablets according to the examples of the present invention.

DESCRIPTION OF EMBODIMENTS

A film-coated orally disintegrating tablet according to the present invention is described below. However, the film-coated orally disintegrating tablet of the present invention should not be interpreted so as to be limited to described contents included in embodiments and examples shown below.

The inventors of the present invention have found that a film for an orally disintegrating tablet excellent in quickly dissolving property, homogeneity, and spreadability is mixed hypromellose and hydroxypropyl cellulose without addition of a plasticizer.

Further, the inventors have found that a film mixed the hypromellose and the hydroxypropyl cellulose has spreadability which is superior to a film added with a plasticizer.

The film-coated orally disintegrating tablet according to the present invention includes an orally disintegrating tablet coated with a composition for film coating containing the hypromellose and the hydroxypropyl cellulose and not containing a plasticizer.

In this embodiment, the composition for film coating does not contain a plasticitier. As a common plasticizer, for example, triethyl citrate, glyceryl fatty acid ester, triacetin, propylene glycol, macrogoal (polyethylene glycol), glyceryl monostearate, or the like can be exemplified, and the composition for film coating in this embodiment does not contain these plasticizers.

In this embodiment, the composition for film coating contains both the hypromellose and the hydroxypropyl cellulose. Also as shown in comparative examples described later, a composition for film coating containing only either the hypromellose or the hydroxypropyl cellulose is problematic.

For example, in an orally disintegrating tablet coated with a composition for film coating containing hypromellose only, a crack occurs in the film. On the other hand, in an orally disintegrating tablet coated with a composition for film coating containing hydroxypropyl cellulose only, sticking between orally disintegrating tables after coated with the film occurs. Further, the tablet after storage under humidification absorbs moisture to be sticky, which is undesirable.

In the composition for film coating according to this embodiment, the hydroxypropyl cellulose is preferably contained in the composition in a range of less than 1:20 in a weight ratio when the hypromellose is 1. Further, the hydroxypropyl cellulose is more preferably contained in a range of 1:4 or less in a weight ratio when the hypromellose is 1. In addition, the hypromellose is preferably contained in the composition in a range of less than 20:1 in a weight ratio when the hydroxypropyl cellulose is 1. Further, the blending ratio of the hypromellose and the hydroxypropyl cellulose is more preferably in a range from 4:1 to 1:4 in a weight ratio.

In the film-coated orally disintegrating tablet according to the present invention, titanium oxide may be contained in the composition for film coating.

In this embodiment, a blending ratio in a case where the titanium oxide is contained in the composition for film coating is preferably 23.4% by weight or less to the total weight of the hypromellose and the hydroxypropyl cellulose. If the composition contains the titanium oxide in a ratio of 46.9% by weight or more, the film becomes easy to crack, which is undesirable.

In the composition for film coating according to the present invention, at least one pharmaceutically acceptable diluent, disintegrator, lubricant, flavoring agent, sweetener and coloring agent commonly used can be further contained.

As the diluent, water-soluble saccharide is preferred, and for example, erythritol, D-mannitol, lactose hydrate, xylitol, isomalt, maltose, and the like can be used, but the diluent is not limited to these diluents. Further, in the composition for film coating according to the present invention, two or more kinds of diluents can be added in combination.

The disintegrator added to the composition for film coating according to the present invention may be any pharmaceutically acceptable disintegrator. As the disintegrator added to the composition for film coating according to the present invention, for example, crospovidone, sodium carboxymethyl starch, croscarmellose sodium, low substituted hydroxy-propylcellulose (also referred to as L-HPC), and the like can be used, but the disintegrator is not limited to these disintegrators.

The lubricant added to the composition for film coating according to the present invention may be any pharmaceutically acceptable lubricant. As the lubricant added to the composition for film coating according to the present invention, for example, talc, light anhydrous silicic acid, magnesium stearate, calcium stearate, sodium stearyl fumarate, sucrose fatty acid ester, or the like can be used, but the lubricant is not limited to these lubricants.

The flavoring agent added to the composition for film coating according to the present invention may be any pharmaceutically acceptable flavoring agent. As the flavoring agent added to the composition for film coating according to the present invention, for example, erythritol, saccharin sodium, dipotassium glycyrrhizinate, stevia, thaumatin, citric acid, or the like can be used, but the flavoring agent is not limited to these flavoring agents.

The sweetener added to the composition for film coating according to the present invention may be any pharmaceutically acceptable sweetener. As the sweetener added to the composition for film coating according to the present invention, for example, sugar such as sucrose, lactose, or glucose, sugar alcohol such as mannitol, xylitol, or sorbitol, sucralose, aspartame, acesulfame potassium, thaumatin, or the like can be used, but the sweetener is not limited to these sweeteners.

The coloring agent added to the composition for film coating according to the present invention may be any pharmaceutically acceptable coloring agent. As the coloring agent added to the composition for film coating according to the present invention, for example, metal oxide such as magnesium oxide, zinc oxide, aluminium oxide, anatase-type or rutile-type titanium oxide, iron sesquioxide, or yellow iron sesquioxide, water-soluble edible tar dye such as Food Yellow No. 5, or Food Blue No. 2 can be used, but the coloring agent is not limited to these coloring agents.

As the solvent used in the composition for film coating, a solvent generally used for film coating of a tablet can be used. For example, a solvent such as purified water or ethanol usually used in a composition for film coating can be used, and solvents can be appropriately mixed and used.

The composition for film coating coats an uncoated orally disintegrating tablet in a common amount used for an orally disintegrating tablet. Preferably, coating of 5% by weight or less to the whole tablet, which does not prevent the orally disintegrating property of the tablet, is performed. More preferably, coating of 3% by weight or less to the whole tablet is performed. Further, more preferably, coating of 2.5% by weight or less to the whole tablet is performed.

The orally disintegrating tablet coated with a film of this embodiment is an oral solid preparation that quickly disintegrates intraorally in about 30 seconds or in a time less than 30 seconds only with intraoral saliva or with a small amount of water.

The orally disintegrating tablet coated with a film of this embodiment is not particularly limited, but is a common orally disintegrating tablet. Further, a producing method of the orally disintegrating tablet can also use a known technique and is not particularly limited.

A uncoated tablet of the orally disintegrating tablet coated with a film of this embodiment can be added with a pharmaceutically acceptable additive agent, as necessary. As the additive agent, for example, an additive agent such as antioxidant, diluent, binder, disintegrator, corrigent, lubricant or the like can be added.

As the antioxidant, for example, butylhydroxyanisole (BHA), dibutylhydroxytoluene (BHT), ascorbic acid, sodium ascorbate, erythorbic acid, sodium erythorbate, tocopherol, propyl gallate, guaiac resin, nordihydroguaiaretic acid, sodium pyrosulfite, sodium bisulfite, rongalit, or the like is cited. These antioxidants can be used alone or in combination of two or more of these antioxidants.

The diluent can be selected from, for example, sugar derivative, starch derivative, cellulose derivative, gum arabic, dextran, pullulan, silicate derivative, phosphate, carbonate, sulfate, or the like. As the sugar derivative, for example, lactose, white sugar, glucose, mannitol, erythritol, trehalose, maltose, xylitol, solbitol, or the like can be cited. Further, as the starch derivative, corn starch, potato starch, α-starch, dextrin, or the like can be cited. As the cellulose derivative, crystalline cellulose or the like can be cited. As the silicate derivative, light anhydrous slicicic acid, synthetic aluminum silicate, calcium silicate, magnesium aluminometasilicate, or the like can be cited. As the phosphate, calcium hydrogen phosphate or the like can be cited. As the carbonate, calcium carbonate, magnesium carbonate, sodium bicarbonate, or the like can be cited. As the sulfate, calcium salfate, or the like can be cited. These diluents can be used alone or in combination of two or more of these diluents.

As the binder, for example, polyvinylpyrrolidone, polyvinyl alcohol, a compounds shown above as the diluent, or the like can be selected. These binders can be used alone or in combination of two or more of these binders.

The disintegrator can be selected from, for example, crospovidone, carmellose calcium, carmellose sodium, croscarmellose sodium, carmellose, cross-linked polyvinylpyrrolidone, low substituted hydroxypropyl cellulose, various starches, or the like. These disintegrator can be used alone or in combination of two or more of these disintegrators.

The corrigent can be selected from, for example, sweetener, acidulant, flavor, or the like. As the sweetener, saccharin sodium, scralose, thaumatin, acesulfame photassium, stevia extract, white sugar, aspartame, or the like can be cited. As the acidulant, citric acid, malic acid, tartaric acid, or the like can be cited. As the flavor, menthol, lemon extract, orange extract, or the like can be cited. These corrigents can be used alone or in combination of two or more of these corrigents.

The lubricant can be selected from, for example, stearic acid, metallic stearate (calcium stearate, magnesium stearate, or the like), talc, colloidal silica, waxes (beadswax, spermaceti, and the like), boric acid, adipic acid, sulfate (sodium sulfate or the like), glycol, fumaric acid, sodium stearyl fumarate, sodium benzoate, D,L-leucine, lauryl sulfate, (sodium lauryl sulfate, magnesium lauryl sulfate or the like), acids (silicic acid anhydride, silicic acid hydrate, or the like), a compound shown above as the diluent, and the like. These lubricants can be used alone or in combination of two or more of these lubricants.

As described above, the present invention can provide an orally disintegrating tablet coated with a film excellent in quickly dissolving property, homogeneity, and spreadability by containing the hypromellose and the hydroxypropyl cellulose without the plasticizer added.

Further, the present invention can provide an orally disintegrating tablet coated with a film excellent in spreadability by blending the titanium oxide in a ratio of 23.4% by weight or less to the total weight of the hydromellose and the hydroxypropyl cellulose in the composition for film coating.
(Producing Method)

A composition for film coating is prepared by, though not particularly limited to, dissolving a film coating base in a mixed solvent of water and ethanol. At this time, at least one pharmaceutically acceptable additive agent of the diluent, the disintegrator, the lubricant, the flavoring agent, and the coloring agent can be further added.

A method for applying film coating to an uncoated orally disintegrating tablet (plain tablet) is not particularly limited and can be performed by putting an uncoated orally disintegrating tablet into a coating machine or a sugar-coating pan commonly used and adding the composition for film coating according to the present invention.
(Increasing Rate of Thickness of Orally Disintegrating Tablet Under High Humidity)

An increasing rate of a thickness of an orally disintegrating tablet under high humidity is calculated by storing a film-coated orally disintegrating tablet under high humidity and measuring thicknesses of the orally disintegrating tablet before and after the storage. For storage at 25° C. and 75% RH, an environmental tester (THG062FA manufactured by ADVANTEC CORPORATION) can be used.

In storage at 25° C. and 90% RH, an environmental tester (desktop constant temperature and humidity reservoir LH21-11M manufactured by NAGANO SCIENCE CO., LTD.) can be used. In measuring the thicknesses of the tablet before and after the storage, a thickness measuring machine (THICKNESS GAUGE manufactured by Mitsutoyo Corporation) can be used.
(Film Crack)

A film crack in the film-coated orally disintegrating tablet is confirmed visually.
(Intraoral Dissolution Time of Film)

The intraoral dissolution time of the film is measured as a time (seconds) from when a healthy adult put the tablet into his/her mouth without taking water until he/she felt that a film layer had dissolved in saliva without biting the tablet and the plain tablet had been exposed.

EXAMPLES

Specific examples and testing results of the film-coated orally disintegrating tablets according to the present invention described above are shown and described in more detail.
(Production Example of an Uncoated Orally Disintegrating Tablet)

A mixture product for tableting was prepared by mixing 990.0 g of mixture of D-mannitol, carmellose, crystalline cellulose, and crospovidone (Granfiller D (registered trademark) GNF-D211, Nichirin Chemical Industries, Ltd./Gotoku Chemical Company Ltd.), and magnesium stearate of 10.0 g (vegetative, by Taihei Chemical Industrial Co., Ltd.). An uncoated orally disintegrating tablet was obtained by using a tableting machine (VELA5, KIKUSUI SEISAKUSHO LTD.) and tableting the mixture product for tableting so as to achieve a weight of 158 mg and a hardness of 3.5 kg.

Example 1

A composition for film coating was obtained by dissolving and dispersing hypromellose (TC-5(registered trademark)M, Shin-Etsu Chemical Co., Ltd.), hydroxypropyl cellulose (HPC-L, NIPPON SODA CO., LTD.), talc (FUJI TALC INDUSTRIAL CO., LTD.), titanium oxide (KA-10M, Titan kogyo, Ltd.), erythritol (Nikken Kasei Co., Ltd.), and scuralose (P, San-Ei Gen F. F. I., Inc.) in a solvent mixed in a ratio of water:ethanol=3:7 so as to achieve a concentration of 8.0% by weight in the blending ratio shown in FIG. 1B. An uncoated orally disintegrating tablet was prepared according to the production example, and a 161.4 mg film-coated orally disintegrating tablet of Example 1 was obtained by coating the uncoated orally disintegrating tablet with the composition for film coating so as to achieve a predetermined weight by using a coating machine (HC-LABO20, Freund Corp.).

Example 2

In Example 1, the hypromellose and the hydroxypropyl cellulose were mixed in the composition for film coating such that the blending ratio of the hypromellose to the hydroxypropyl cellulose was 4:1 by weight, but, in Example 2, the hypromellose and the hydroxypropyl cellulose were mixed in the composition for film coating such that the blending ratio of the hypromellose to the hydroxypropyl cellulose was 1:1 by weight. A 161.4 mg film-coated orally disintegrating tablet of Example 2 was obtained by mixing each additive agent in a solvent mixed in a ratio of water:ethanol=3:7 so as to achieve a concentration of 8.0% by weight in the blending ratio shown in FIG. 1B and carrying out production in the same manner as Example 1.

Example 3

In Example 1, the hypromellose and the hydroxypropyl cellulose were mixed in the composition for film coating such that the blending ratio of the hypromellose to the hydroxypropyl cellulose was 4:1 by weight, but, in Example 3, the hypromellose and the hydroxypropyl cellulose were mixed in the composition for film coating such that the blending ratio of the hypromellose to the hydroxypropyl cellulose was 1:4 by weight. A 161.4 mg film-coated orally disintegrating tablet of Example 3 was obtained by mixing each additive agent in a solvent mixed in a ratio of water:ethanol=3:7 so as to achieve a concentration of 8.0% by weight in the blending ratio shown in FIG. 1B and carrying out production in the same manner as Example 1.

Example 4

In Example 1, the hypromellose and the hydroxypropyl cellulose were mixed in the composition for film coating such that the blending ratio of the hypromellose to the hydroxypropyl cellulose was 4:1 by weight, but, in Example 4, the hypromellose and the hydroxypropyl cellulose were mixed in the composition for film coating such that the blending ratio of the hypromellose to the hydroxypropyl cellulose was 20:1 by weight. A 161.4 mg film-coated orally disintegrating tablet of Example 4 was obtained mixing each additive agent in a solvent mixed in a ratio of water:ethanol=3:7 so as to achieve a concentration of 8.0% by weight in the blending ratio shown in FIG. 1B and carrying out production in the same manner as Example 1.

Example 5

In Example 1, the hypromellose and the hydroxypropyl cellulose were mixed in the composition for film coating such that the blending ratio of the hypromellose to the hydroxypropyl cellulose was 4:1 by weight, but, in Example 5, the hypromellose and the hydroxypropyl cellulose were mixed in the composition for film coating such that the blending ratio of the hypromellose to the hydroxypropyl cellulose was 1:20 by weight. A 161.4 mg film-coated orally disintegrating tablet of Example 5 was obtained mixing each additive agent in solvent mixed in a ratio of water:ethanol=3:7 so as to achieve a concentration of 8.0% by weight in the blending ratio shown in FIG. 1B and carrying out production in the same manner as Example 1.

Example 6

In Example 1, titanium oxide was mixed in the composition for film coating in a ratio of 1.3% by weight to the total weight of the hypromellose and the hydroxypropyl cellulose, but, in Example 6, titanium oxide was mixed in the composition for film coating so as to be in a ratio of 5.9% by weight to the total weight of the hypromellose and the hydroxypropyl cellulose. A 161.53 mg film-coated orally disintegrating tablet of Example 6 was obtained by mixing each additive agent in solvent mixed in a ratio of water:ethanol=3:7 so as to achieve a concentration of 8.3% by weight in the blending ratio shown in FIG. 2 and carrying out production in the same manner as Example 1.

Example 7

In Example 1, titanium oxide was mixed in the composition for film coating in a ratio of 1.3% by weight to the total weight of the hypromellose and the hydroxypropyl cellulose, but, in Example 7, titanium oxide was mixed in the composition for film coating so as to be in a ratio of 11.7% by weight to the total weight of the hypromellose and the hydroxypropyl cellulose. A 161.7 mg film-coated orally disintegrating tablet of Example 7 was obtained by mixing each additive agent in a solvent mixed in a ratio of water:ethanol=3:7 so as to achieve a concentration of 8.7% by weight in the blending ratio shown in FIG. 2 and carrying out production in the same manner as Example 1.

Example 8

In Example 1, titanium oxide was mixed in the composition for film coating in a ratio of 1.3% by weight to the total weight of the hypromellose and the hydroxypropyl cellulose, but, in Example 8, titanium oxide was mixed in the composition for film coating so as to be in a ratio of 23.4% by weight to the total weight of the hypromellose and the hydroxypropyl cellulose. A 162.04 mg film-coated orally disintegrating tablet of Example 8 was obtained by mixing each additive agent in a solvent mixed in a ratio of water:ethanol=3:7 so as to achieve a concentration of 9.5% by weight in the blending ratio shown in FIG. 2 and carrying out production in the same manner as Example 1.

Comparative Example 1

In Example 1, the hypromellose and the hydroxypropyl cellulose were mixed in the composition for film coating such that the blending ratio of the hypromellose to the hydroxypropyl cellulose was 4:1 by weight, but, in Comparative Example 1, the hydroxypropyl cellulose was not added in the composition for film coating, but propylene glycol was added thereto, such that the the hypromellose and the propylene glycol were mixed such that the blending ratio of the hypromellose to propylene glycol was 10:3 by weight. A 161.4 mg film-coated orally disintegrating tablet of Comparative Example 1 was obtained by mixing each additive agent in a solvent mixed in a ratio of water:ethanol=3:7 so as to achieve a concentration of 8.0% by weight in the blending ratio shown in FIG. 1A and carrying out production in the same manner as Example 1.

Comparative Example 2

In Example 1, the hypromellose and the hydroxypropyl cellulose were mixed in the composition for film coating such that the blending ratio of the hypromellose to the hydroxypropyl cellulose was 4:1 by weight, but in Comparative Example 2, the propylene glycol was further added to the composition for film coating containing the hypromellose and the hydroxypropyl cellulose, and the hypromellose, the hydroxypropyl cellulose, and the propylene glycol were mixed such that the blending ratio of the hypromellose:the hydroxypropyl cellulose:the propylene glycol was 10:3:2 by weight. A 161.4 mg film-coated orally disintegrating tablet of Comparative Example 2 was obtained by mixing each additive agent in a solvent mixed in a ratio of water:ethanol=3:7 so as to achieve a concentration of 8.0% by weight in the blending ratio shown in FIG. 1A and carrying out production in the same manner as Example 1.

Comparative Example 3

In Example 1, the hypromellose and the hydroxypropyl cellulose were mixed in the composition for film coating such that the blending ratio of the hypromellose to the hydroxypropyl cellulose was 4:1 by weight, but, in Comparative Example 3, the hydroxypropyl cellulose was not added to the composition for film coating, and only the hypromellose was mixed therein. A 161.4 mg film-coated orally disintegrating tablet of Comparative Example 3 was obtained by mixing each additive agent in a solvent mixed in a ratio of water:ethanol=3:7 so as to achieve a concentration of 8.0% by weight in the blending ratio shown in FIG. 1A and carrying out production in the same manner as Example 1.

Comparative Example 4

In Example 1, the hypromellose and the hydroxypropyl cellulose were mixed in the composition for film coating such that the blending ratio of the hypromellose to the hydroxypropyl cellulose was 4:1 by weight, but, in Comparative Example 4, the hypromellose was not added to the composition for film coating, and only the hydroxypropyl cellulose was mixed therein. A 161.4 mg film-coated orally disintegrating tablet of Comparative Example 4 was obtained by mixing each additive agent in a solvent mixed in a ratio of water:ethanol=3:7 so as to achieve a concentration of 8.0% by weight in the blending ratio shown in FIG. 1A and carrying out production in the same manner as Example 1.

Comparative Example 5

In Example 1, titanium oxide was blended in the composition for film coating in a ratio of 1.3% by weight to the total weight of the hypromellose and the hydroxypropyl cellulose, but, in Comparative Example 5, titanium oxide was blended in the composition for film coating so as to be in a ratio of 46.9% by weight to the total weight of the hypromellose and the hydroxypropyl cellulose. A 162.72 mg film-coated orally disintegrating tablet of Comparative Example 5 was obtained by mixing each additive agent in a solvent mixed in a ratio of water:ethanol=3:7 so as to achieve a concentration of 11.1% by weight in the blending ratio shown in FIG. 2 and carrying out production in the same manner as Example 1.

Comparative Example 6

In Example 1, titanium oxide was blended in the composition for film coating in a ratio of 1.3% by weight to the total weight of the hypromellose and the hydroxypropyl cellulose, but, in Comparative Example 6, titanium oxide was blended in the composition for film coating so as to be in a ratio of 58.6% by weight to the total weight of the hypromellose and the hydroxypropyl cellulose. A 163.06 mg film-coated orally disintegrating tablet of Comparative Example 6 was obtained by mixing each additive agent in a solvent mixed in a ratio of water:ethanol=3:7 so as to obtain a concentration of 12.0% by weight in the blending ratio shown in FIG. 2 and carrying out production in the same manner as Example 1.

FIG. 1A is tables showing formulations of compositions for film coating and physical properties or the like of film-coated orally disintegrating tablets according to the examples of the present invention. FIG. 1B is tables showing formulations of compositions for film coatings and physical properties or the like of preparations of film-coated orally disintegrating tablets according to examples of the present invention.

(Increasing Rate of Thickness of Orally Disintegrating Tablet Under High Humidity)

An increasing rate of a thickness of an orally disintegrating tablet under high humidity was calculated as an increasing rate (%) obtained by storing a film-coated orally disintegrating tablet for 16 hours at 25° C. under a relative humidity of 75% and then measuring thicknesses of the tablet before and after storage by using a thickness measuring machine (thickness gage, Mitsutoyo Corporation).

(Crack in Film)

A crack of a film of a film-coated orally disintegrating tablet was visually confirmed after the film-coated orally disintegrating tablet was stored for 16 hours at 25° C. under a relative humidity of 75%.

(Intraoral Dissolution Time of Film)

The intraoral dissolution time of a film was measured as a time (seconds) from when a healthy adult put the tablet into his/her mouth without taking water until he/she felt that a film layer has dissolved in saliva without biting the tablet and the plain tablet had been exposed.

Comparative Example 1 and Comparative Example 2 are the film-coated orally disintegrating tablets containing propylene glycol as a plasticizer in the composition for film coating. Both Comparative Example 1 and Comparative Example 2 have appropriate intraoral dissolution time as an orally disintegrating tablet, but a crack of the film due to the increase in thickness of the orally disintegrating tablet under high humidity was confirmed.

Comparative Example 3 is a preparation not containing propylene glycol as a plasticizer in the composition for film coating but containing only the hypromellose as a film base. Comparative Example 3 has appropriate intraoral dissolution time as an orally disintegrating tablet, but a crack of the film due to the increasing in thickness of the orally disintegrating tablet under high humidity was confirmed.

Comparative Example 4 is a preparation not containing propylene glycol as a plasticizer in the composition for film coating but containing only the hydroxypropyl cellulose as a film base. Comparative Example 4 has appropriate intraoral dissolution time as an orally disintegrating tablet, but pairing (sticking together) of the tablets after produced occurred. In addition, in the tablet after storage under humidification, the fact that the film which has absorbed moisture no longer has a function as a film was confirmed.

On the other hand, Example 1 to Example 5 are preparations containing the hypromellose and the hydroxypropyl cellulose in the blending ratios of 4:1, 1:1, 1:4, 20:1, 1:20 by weight, respectively, and not containing proplylene glycol as a plasticizer in the composition for film coating. All of the films of the orally integrating tablets of Example 1 to Example 5 have appropriate intraoral dissolution times as an orally integrating tablet, and regardless of the increase in thickness of the orally disintegrating tablet due to storage under high humidity, a crack of the film was not confirmed. The intraoral dissolution time of the film of the orally disintegrating tablet of Example 4 was 8 to 10 seconds, which was slightly slow as compared with the fact that the intraoral dissolution time of film of the orally disintegrating tablets of Example 1 to Example 3 and Example 5, was 5 to 8 seconds. Further, in the preparations of Example 5, pairing of only a few tablets after produced occurred because the composition for film coating is sticky.

Thus, the film containing the hypromellose and the hydroxypropyl cellulose but not containing a plasticizer quickly dissolves in the mouth and does not suppress the disintegrating property of the orally disintegrating tablet. Further, since the film has such excellent spreadability so as to endure swelling of the tablet due to absorption of moisture, the film is difficult to crack even when the film is put in a severe environment after coating.

In addition, since the film does not contain a plasticizer, the film can also be used in an orally disintegrating tablet containing drug substance unstable to a plasticizer, so that a film-coated orally disintegrating tablet short in dissolution time, excellent in spreadability, and excellent in versatility can be provided.

FIG. 2 is tables showing physical properties or the like of the film-coated orally disintegrating tablets according to the examples of the present invention.
(Increasing Rate of Thickness of Orally Disintegrating Tablet Under High Humidity)

The increase rate of a thickness of an orally disintegrating tablet under high humidity was calculated as an increasing rate (%) obtained by storing a film-coated orally disintegrating tablet for 5 hours at 25° C. under a relative humidity of 90% and then measuring thicknesses of the tablet before and after storage by using a thickness measuring machine (THICKNESS GAGE, Mitsutoyo Corporation).
(Cracking in Film)

A crack of a film of a film-coated orally disintegrating tablet was visually confirmed after the film-coated orally disintegrating tablet was stored for 5 hours at 25° C. under a relative humidity of 90%.
(Intraoral Dissolution Time of Film)

Since the measuring method of the intraoral dissolution time is similar to the above-described measuring method, detailed description thereof is omitted.

Example 4 to Example 6 are preparations containing titanium oxide in ratios of 5.9% by weight, 11.7% by weight, and 23.4% by weight respectively, to the total weight of the hypromellose and the hydroxypropyl cellulose, in the compositions for film coating, but all of Example 4 to Example 6 have appropriate intraoral dissolution time as an orally disintegrating tablet, and, regardless of the increase in thickness of the orally disintegrating tablet due to storage under high humidity, a crack of the film was not confirmed.

On the other hand, Comparative Example 5 and Comparative Example 6 where the blending ratio of the titanium oxide was further increased are preparations containing titanium oxide in ratios of 46.9% by weight, 58.6% by weight, respectively, to the total weight of the hypromellose and the hydroxypropyl cellulose, in the compositions for film coating, and both Comparative Example 5 and Comparative Example 6 have appropriate intraoral dissolution time as an orally disintegrating tablet, but a crack of the film due to the increase in thickness of the orally disintegrating tablet under high humidity was confirmed.

Thus, generally, when the titanium oxide added as a coloring agent is blended, the spreadability of the film deteriorates, but a preparation containing the titanium oxide in a ratio of 23.4% by weight or less to the total weight of the hypromellose and the hydroxypropyl cellulose has such excellent spreadability so as to endure swelling of the tablet due to absorption of moisture, so that a film-coated orally disintegrating tablet where the film is difficult to crack even when the film is put in a severe environment after coated, the dissolution time is short, the spreadability is excellent and the versatility is excellent can be provided.

As described above, since the film-coated orally disintegrating tablet according to the present invention is is coated with the composition for film coating containing hypromellose and hydroxypropyl cellulose but not containing a plasticizer, a film-coated orally disintegrating tablet short in dissolution time, excellent in spreadability, and excellent in versatility can be provided.

According to the present invention, a film-coated orally disintegrating tablet is provided. According to the present invention, in particular, a film-coated orally disintegrating tablet that is short in dissolution time, is excellent in spreadability, and is excellent in versatility is provided.

Further, since the film coating provided by the present invention does not contain a plasticizer, the film coating can also be used in a tablet containing an active ingredient whose storage stability is impaired by coming in contact with a plasticizer.

What is claimed is:
1. A film-coated orally disintegrating tablet comprising:
an uncoated orally disintegrating tablet including one or more pharmaceutically acceptable additive agent; and
a film arranged on the uncoated orally disintegrating tablet, the film consisting of a composition for film coating,
wherein
the composition for film coating consists of hypromellose and hydroxypropyl cellulose, a flavoring agent, a diluent, a disintegrator, a lubricant, a sweetener and a coloring agent without containing plasticizer,
the flavoring agent is at least one selected from the group consisting of erythritol, saccharin sodium, dipotassium glycyrrhizinate, stevia, thaumatin and citric acid,
an amount of the composition for film coating is 2% by weight or more and 3% by weight or less based on an amount of the film-coated orally disintegrating tablet, and
a blending ratio of the hypromellose to the hydroxypropyl cellulose in the composition for film coating is from 20:1 to 4:1 in a weight ratio.
2. The film-coated orally disintegrating tablet according to claim 1 further comprising titanium oxide in a ratio of 23.4% by weight or less to a total weight of the hypromellose and the hydroxypropyl cellulose.

* * * * *